United States Patent
Jones et al.

(10) Patent No.: US 9,757,243 B2
(45) Date of Patent: Sep. 12, 2017

(54) INTERCONDYLAR COMPONENT AND FIN ATTACHMENT FEATURES FOR USE IN KNEE ARTHROPLASTY

(71) Applicant: Zimmer, Inc., Warsaw, IN (US)

(72) Inventors: Nolan C. Jones, Warsaw, IN (US); Shanon N. Roberts, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/749,908

(22) Filed: Jun. 25, 2015

(65) Prior Publication Data
US 2016/0008136 A1    Jan. 14, 2016

Related U.S. Application Data

(60) Provisional application No. 62/021,976, filed on Jul. 8, 2014, provisional application No. 62/063,497, filed on Oct. 14, 2014.

(51) Int. Cl.
*A61F 2/38* (2006.01)
*A61F 2/30* (2006.01)

(52) U.S. Cl.
CPC .... *A61F 2/389* (2013.01); *A61F 2002/30013* (2013.01); *A61F 2002/3092* (2013.01);
(Continued)

(58) Field of Classification Search
CPC ............ A61F 2/389; A61F 2002/30013; A61F 2002/30884
See application file for complete search history.

(56) References Cited

U.S. PATENT DOCUMENTS

| | | |
|---|---|---|
| 3,728,742 A | 4/1973 | Averill et al. |
| 3,816,855 A | 6/1974 | Saleh |

(Continued)

FOREIGN PATENT DOCUMENTS

| | | |
|---|---|---|
| EP | 0672397 A1 | 9/1995 |
| FR | 2737970 | 2/1997 |

(Continued)

OTHER PUBLICATIONS

"U.S. Appl. No. 14/487,730, Non Final Office Action mailed Jun. 28, 2016", 10 pgs.

(Continued)

*Primary Examiner* — Brian Dukert
(74) *Attorney, Agent, or Firm* — Schwegman Lundberg & Woessner, P.A.

(57) ABSTRACT

Tibial prosthesis having one or more fins for use in a total or unicompartmental knee athroplasty procedure are disclosed. The one or more fins can be adapted to fix a tibial prosthesis to the tibia and can engage with corresponding channels formed in the resected tibia. Additionally, intercondylar components and methods for use in a total or unicompartmental knee athroplasty procedure are disclosed. The intercondylar component can be integral with or attached to a baseplate configured for attachment to a partially resected proximal surface of the tibia that retains at least a portion of the intercondylar eminence and the anterior cruciate ligament (ACL) and/or the posterior cruciate ligament (PCL). Inner surfaces of the intercondylar component can be configured to engage with at least a portion of the intercondylar eminence remaining with the partially resected tibia. In an example, the intercondylar component or the one or more fins can be formed of a porous material, such as to facilitate bone growth.

12 Claims, 13 Drawing Sheets

(52) U.S. Cl.
CPC .......... *A61F 2002/3093* (2013.01); *A61F 2002/30578* (2013.01); *A61F 2002/30879* (2013.01); *A61F 2002/30884* (2013.01); *A61F 2002/3895* (2013.01); *A61F 2310/00131* (2013.01)

(56) References Cited

U.S. PATENT DOCUMENTS

| | | | |
|---|---|---|---|
| 4,728,332 | A | 3/1988 | Albrektsson |
| 5,282,861 | A | 2/1994 | Kaplan |
| 5,282,868 | A | 2/1994 | Bahler |
| 5,824,101 | A | 10/1998 | Pappas |
| 5,954,768 | A | 9/1999 | Lepaih |
| 7,060,101 | B2 | 6/2006 | O'Connor et al. |
| 7,758,652 | B2 | 7/2010 | Engh et al. |
| 7,846,376 | B2 | 12/2010 | Abt et al. |
| 7,918,382 | B2 | 4/2011 | Charlesbois et al. |
| 8,066,776 | B2 | 11/2011 | O'Connor et al. |
| 8,608,049 | B2 | 12/2013 | Hippensteel et al. |
| 8,728,086 | B2 | 5/2014 | Smith et al. |
| 8,864,836 | B2 | 10/2014 | Hodorek |
| 2002/0022890 | A1* | 2/2002 | Jacobsson .......... A61F 2/389 623/18.11 |
| 2004/0039447 | A1 | 2/2004 | Simon et al. |
| 2005/0143831 | A1 | 6/2005 | Justin et al. |
| 2006/0224244 | A1 | 10/2006 | Thomas et al. |
| 2006/0235517 | A1 | 10/2006 | Hodorek |
| 2007/0173858 | A1 | 7/2007 | Engh et al. |
| 2010/0016980 | A1 | 1/2010 | Donno et al. |
| 2011/0190898 | A1 | 8/2011 | Lenz et al. |
| 2011/0264097 | A1 | 10/2011 | Hodorek et al. |
| 2012/0035736 | A1 | 2/2012 | O'Connor et al. |
| 2012/0125896 | A1 | 5/2012 | Vargas et al. |
| 2012/0310361 | A1 | 12/2012 | Zubok et al. |
| 2013/0197527 | A1 | 8/2013 | Nadzadi et al. |
| 2014/0296990 | A1* | 10/2014 | Shaw .......... A61F 2/389 623/20.21 |
| 2015/0005889 | A1 | 1/2015 | Hodorek et al. |

FOREIGN PATENT DOCUMENTS

| | | |
|---|---|---|
| WO | WO-2007090784 A1 | 8/2007 |
| WO | WO-2009158318 A1 | 12/2009 |
| WO | WO-2016007304 A1 | 1/2016 |

OTHER PUBLICATIONS

"U.S. Appl. No. 14/487,730, Preliminary Amendment filed Sep. 16, 2014", 8 pgs.
"U.S. Appl. No. 14/487,730, Response filed Jun. 13, 2016 to Restriction Requirement mailed May 31, 2016", 8 pgs.
"U.S. Appl. No. 14/487,730, Restriction Requirement mailed May 31, 2016", 6 pgs.
"Application Serial No. PCT/US2015/037608, Invitation to Pay Additional Fees and Partial Search Report mailed Sep. 7, 2015", 6 pgs.
"International Application Serial No. PCT/US2015/037608, International Search Report mailed Nov. 24, 2015", 8 pgs.
"International Application Serial No. PCT/US2015/037608, Written Opinion mailed Nov. 24, 2015", 10 pgs.
"U.S. Appl. No. 13/001,442, Examiner Interview Summary mailed Dec. 6, 2013", 3 pgs.
"U.S. Appl. No. 13/001,442, Final Office Action mailed Aug. 30, 2013", 8 pgs.
"U.S. Appl. No. 13/001,442, Non Final Office Action mailed Apr. 29, 2013", 7 pgs.
"U.S. Appl. No. 13/001,442, Notice of Allowance mailed Jun. 24, 2014", 7 pgs.
"U.S. Appl. No. 13/001,442, Response filed Apr. 15, 2013 to Restriction Requirement mailed Feb. 15, 2013", 12 pgs.
"U.S. Appl. No. 13/001,442, Response filed Jul. 29, 2013 to Non Final Office Action mailed Apr. 29, 2013", 17 pgs.
"U.S. Appl. No. 13/001,442, Response to Final Office Action dated Aug. 30, 2013 filed Dec. 2, 2013", 17 pgs.
"U.S. Appl. No. 13/001,442, Restriction Requirement mailed Feb. 15, 2013", 10 pgs.
"Geomedic Total Knee Prothesis", Howmedica, Inc., (1975), 4 pgs.
"International Application Serial No. PCT/US2009/048205, International Preliminary Report on Patentability mailed Jan. 5, 2011", 4 pgs.
"International Application Serial No. PCT/US2009/048205, International Search Report mailed Dec. 11, 2009", 7 pgs.
"International Application Serial No. PCT/US2009/048205, Written Opinion mailed Dec. 27, 2010", 9 pgs.
"The Charnley Cobra, The Charnley Knee Prostheses, The Duo/Patella Knee Prostheses", Cintor, Division of Codman, (1975), 4 pgs.
"The Townley Anatomic Knee Replacement", DePuy, 10 pgs.
Levine, Brett R, et al., "Experimental and clinical performance of porous tantalum in orthopedic surgery", Biomaterials, (27), (Sep. 2006), 4671-81.
Pritchett, James W., "BioPro Equalizer Modular Total Knee Replacement", BioPro, Division of Implant Manufacturing and Testing Inc., 19 pgs.
"U.S. Appl. No. 14/487,730, Notice of Allowance mailed Oct. 25, 2016", 8 pgs.
"U.S. Appl. No. 14/487,730, Response filed Sep. 28, 2016 to Non Final Office Action mailed Jun. 28, 2016", 12 pgs.
"U.S. Appl. No. 14/487,730, Corrected Notice of Allowance mailed Feb. 2, 2017", 4 pgs.
"U.S. Appl. No. 15/427,280, Preliminary Amendment filed Mar. 8, 2017", 7 pgs.
"International Application Serial No. PCT/US2015/037608, International Preliminary Report on Patentability mailed Jan. 19, 2017", 12 pgs.

* cited by examiner

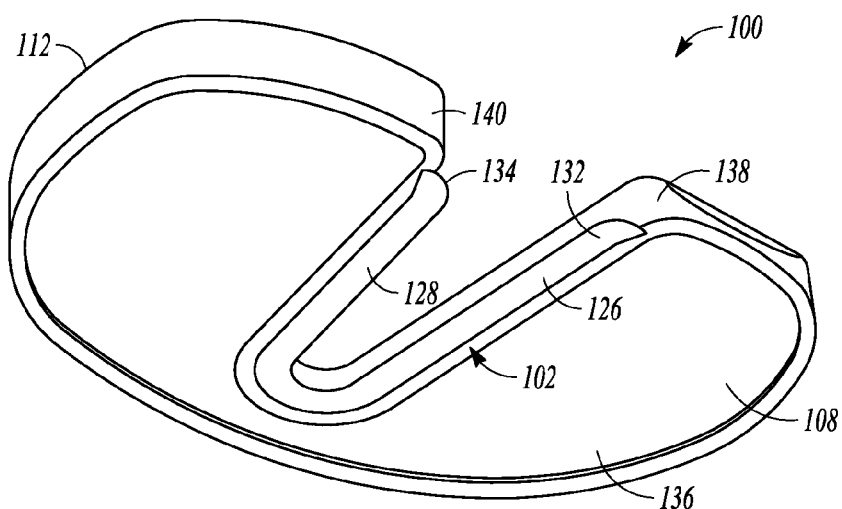
FIG. 3C
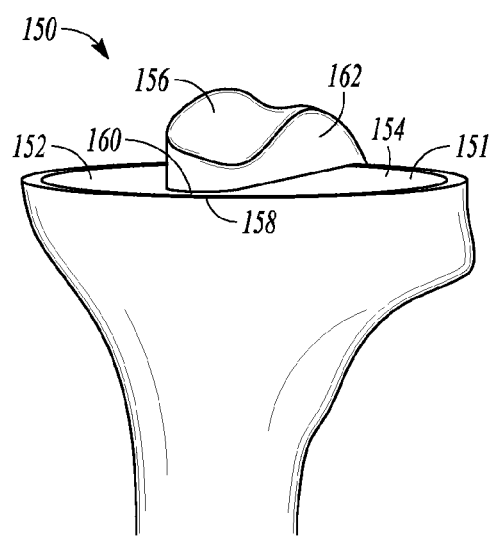  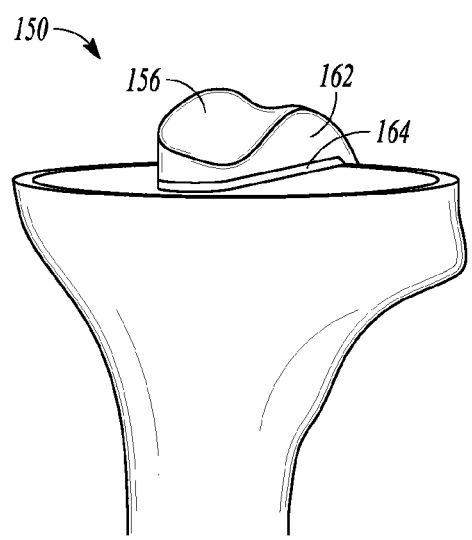
FIG. 4A                FIG. 4B

INTERCONDYLAR COMPONENT AND FIN ATTACHMENT FEATURES FOR USE IN KNEE ARTHROPLASTY

CLAIM OF PRIORITY

This application claims the benefit of U.S. Provisional Patent Application Ser. No. 62/021,976, filed on Jul. 8, 2014, and also claims the benefit of U.S. Provisional Patent Application Ser. No. 62/063,497, filed on Oct. 14, 2014, the benefit of priority of each of which is claimed hereby, and each of which are incorporated by reference herein in its entirety.

TECHNICAL FIELD

The present application relates to orthopedic prostheses, and more particularly, to components such as an intercondylar component and/or fin(s) for use with a tibial implant in a total knee or a unicompartmental knee arthroplasty procedure.

BACKGROUND

Orthopedic procedures are commonly utilized to repair and/or replace damaged bone and tissue in the human body. For example, a knee prosthesis may be used to restore natural knee function by repairing damaged or diseased articular surfaces of the femur and/or tibia. Knee prostheses may include a femoral component implanted on the distal end of the femur, which articulates with a tibial component implanted on the proximal end of the tibia to replicate the function of a healthy natural knee.

In a total knee arthroplasty (TKA) procedure, the intercondylar eminence or raised area between the medial and lateral compartments of the tibia is typically sacrificed along with the anterior cruciate ligament (ACL), in part, to accommodate the tibial prosthesis. It may be advantageous to maintain a portion of the intercondylar eminence and the ACL, particularly if a revision surgery is later needed.

OVERVIEW

The present inventors recognize, among other things, an opportunity for an intercondylar component attachable to a tibial implant configured for use with a partially resected tibia, retaining at least a portion of the intercondylar eminence and the ACL and/or posterior cruciate ligament (PCL). The intercondylar component described herein can be used with a tibial implant configured for use in a total knee arthroplasty procedure or with a tibial implant configured for use in a unicompartmental arthroplasty procedure.

The present inventors further recognize that one or more fins can be attachable to or integrally formed with the tibial implant to provide for fixation to the tibia in order to better address forces on the tibial implant such as a lift off moment and/or a rotation in the coronal plane. The fin(s) described herein can be used with a tibial implant configured for use in a total knee arthroplasty procedure or with a tibial implant configured for use in a unicompartmental arthroplasty procedure and can be used with or without the intercondylar component described herein.

To further illustrate the components and methods disclosed herein, a non-limiting list of examples is provided here:

In Example 1, a tibial implant configured for attachment to a tibia in a knee arthroplasty can comprise a baseplate configured for attachment to a partially resected proximal surface of the tibia and an intercondylar component attachable to or integral with the baseplate. The baseplate can comprise a medial compartment, a lateral compartment, and an anterior bridge portion between the medial and lateral compartments such that a notch is formed between an inner surface of the medial compartment and an inner surface of the lateral compartment. The intercondylar component can comprise a medial portion configured to connect to the inner surface of the medial compartment, a lateral portion configured to connect to the inner surface of the lateral compartment, and an arcuate portion between the medial portion and the lateral portion and configured to connect to the bridge portion of the baseplate.

In Example 2, the tibial implant of Example 1 can optionally be configured such that the intercondylar component includes a porous structure.

In Example 3, the tibial implant of Example 2 can optionally be configured such that the porous structure includes tantalum.

In Example 4, the tibial implant of Example 2 can optionally be configured such that substantially an entirety of the intercondylar component is formed of a porous metal structure.

In Example 5, the tibial implant of any one or any combination of Examples 1-4 can optionally be configured such that the baseplate includes a first plate formed of a porous structure and a second plate formed of a metal or polymeric material.

In Example 6, the tibial implant of Example 5 can optionally be configured such that the intercondylar component is integral with the first plate.

In Example 7, the tibial implant of Example 6 can optionally be configured such that the intercondylar component and the first plate are bondable to an underside of the second plate.

In Example 8, the tibial implant of any one or any combination of Examples 1-7 can optionally be configured such that the partially resected proximal surface of the tibia includes at least a portion of an intercondylar eminence of the tibia and at least one of the ACL and PCL, and the intercondylar component engages with the intercondylar eminence when the tibial implant is attached to the tibia.

In Example 9, the tibial implant of any one or any combination of Examples 1-8 can optionally be configured such that one or more openings are formed in one or both of the medial and lateral compartment of the baseplate. The one or more openings can be configured to receive a bone screw for securement of the tibial implant to the resected tibia.

In Example 10, a tibial component configured for attachment to a tibial implant having an elongated cut-out extending from a posterior end toward an anterior end of the implant can comprise a first elongated portion, a second elongated portion, and an arcuate portion between the first and second elongated portions. Outer surfaces of the first and second elongated portions and the arcuate portion can be configured to connect to surfaces of the tibial implant that form the elongated cut-out. Inner surfaces of at least a portion of the first and second elongated portions and the arcuate portion can be configured to engage with at least a portion of an intercondylar eminence remaining after resecting a proximal surface of the tibia.

In Example 11, the tibial component of Example 10 can optionally be configured such that the tibial component is formed of a porous metal.

In Example 12, the tibial component of Example 11 can optionally be configured such that the porous metal is tantalum.

In Example 13, the tibial component of any one or any combination of Examples 10-12 can optionally further comprise a porous plate. The first and second elongated portions and the arcuate portion can be integral with or attachable to the porous plate.

In Example 14, the tibial component of Example 13 can optionally be configured such that the porous plate corresponds in size and shape to the tibial implant.

In Example 15, the tibial component of Example 13 can optionally be configured such that the tibial component is bondable to the tibial implant.

In Example 16, a method of performing a knee arthroplasty can comprise partially resecting a proximal surface of a tibia, while retaining at least a portion of an intercondylar eminence of the tibia and at least one of the ACL and PCL, and attaching a tibial implant to the resected proximal surface of the tibia. The tibial implant can comprise a baseplate having an inferior surface configured to contact the resected proximal surface of the tibia, a medial compartment, a lateral compartment, and an anterior bridge portion connecting the medial and lateral compartments such that the a cut-out is formed between inner surfaces of the medial and lateral compartments. The tibial implant can also comprise an intercondylar component attachable to or integral with the baseplate. The intercondylar component can comprise a first elongated portion configured to connect to the inner surface of the medial compartment of the baseplate, a second elongated portion configured to connect to the inner surface of the lateral compartment of the baseplate, and an arcuate portion between the first and second elongated portions and configured to connect to the bridge portion of the baseplate. The method can further comprise engaging the intercondylar component with at least a portion of the retained intercondylar eminence to promote bone ingrowth.

In Example 17, the method of Example 16 can optionally be configured such that engaging the intercondylar component with at least a portion of the retained intercondylar eminence can include forming a first press fit between the first elongated portion of the intercondylar component and the intercondylar eminence at or near a posterior end of the tibia and forming a second press fit between the second elongated portion of the intercondylar component and the intercondylar eminence at or near the posterior end of the tibia.

In Example 18, the method of any one or any combination of Examples 16 or 17 can optionally be configured such that partially resecting a proximal surface of the tibia can comprise resecting the medial and lateral articular surfaces of the tibia such that at least a portion of the intercondylar eminence remains between a resected surface on the medial side of the tibia and a resected surface on the lateral side of the tibia, and resecting an anterior surface of the tibia between the medial and lateral articular surfaces.

In Example 19, the method of Example 18 can optionally be configured such that the remaining portion of the intercondylar eminence includes side walls forming an exterior surface of the intercondylar eminence having a size and shape configured to correspond with the first and second elongated portions and the arcuate portion of the intercondylar component.

In Example 20, the method of Example 19 can optionally further comprise forming a groove in the side walls of the remaining portion of the intercondylar eminence such that the intercondylar component can be pressed into the groove upon engaging the intercondylar component with the intercondylar eminence.

In Example 21, a tibial implant configured for attachment to a tibia in a unicompartmental knee arthroplasty can comprise a baseplate configured for attachment to a resected medial or lateral compartment of the tibia and an intercondylar component attachable to or integral with the baseplate. The intercondylar component can comprise an inner surface configured to engage with an inner edge of the baseplate and an outer surface configured to engage with an intercondylar eminence of the tibia. The intercondylar component can be formed of a porous metal structure to promote bone ingrowth of the intercondylar eminence and the resected medial or lateral compartment of the tibia.

In Example 22, the tibial implant of Example 21 can optionally be configured such that the baseplate includes a first plate formed of a porous metal structure and a second plate formed of a metal or polymeric material.

In Example 23, the tibial implant of Example 22 can optionally be configured such that the intercondylar component is integral with the first plate. The intercondylar component and the first plate can be bonded to an underside of the second plate.

In Example 24, the tibial implant of Example 21 can optionally include one or more fins configured for attachment of the baseplate to a resected medial or lateral compartment of the tibia.

In Example 25, a tibial implant configured for attachment to a tibia in a knee arthroplasty can comprise a baseplate and one or more fins attachable to or integral with an underside of the baseplate. The one or more fins can be configured for attachment to a partially resected proximal surface of the tibia.

In Example 26, the tibial implant of Example 25 can have the baseplate include a medial side, a lateral side, and an anterior bridge portion. The medial side can have at least one of the one or more fins extending from an underside thereof. The lateral side can have at least one of the one or more fins extending from an underside thereof. The anterior bridge portion can be disposed between the medial and lateral compartments such that a notch is formed between an inner surface of the medial side and an inner surface of the lateral side.

In Example 27, the tibial implant of Example 25 can further include an intercondylar component attachable to or integral with the baseplate along an edge of the notch.

In Example 28, the tibial implant of Example 25 the one or more fins can comprise a porous structure.

In Example 29, the tibial implant of Example 28 the porous structure can include tantalum.

In Example 30, the tibial implant of Example 25 the baseplate can include a first plate formed of a porous structure and a second plate formed of a metal or polymeric material.

In Example 31, the tibial implant of Example 30 the one or more fins can be integral with the first plate.

In Example 32, the tibial implant of Example 31 the one or more fins and the first plate can be bondable to an underside of the second plate.

In Example 33, the tibial implant of Example 25 each of the one or more fins can have a side surface disposed at an acute angle to an underside surface.

In Example 34, the tibial implant of Example 33 the one or more fins can have a generally trapezoidal cross-sectional shape.

In Example 35, the tibial implant of Example 25 the one or more fins can be configured to engage one or more channels along the partially resected proximal surface of the tibia.

In Example 36, the tibial implant of Example 25 the baseplate can comprise only one of a medial side or a lateral side, and the one or more fins extend from an underside of the medial side or the lateral side.

In Example 37, a method of performing a knee arthroplasty can comprise partially resecting a proximal surface of a tibia and inserting a tibial implant to the resected proximal surface of the tibia from an anterior side of the tibia toward a posterior side thereof. The tibial implant can comprise a baseplate having an inferior surface configured to interface with the resected proximal surface of the tibia and one or more fins attachable to or integral with the inferior surface of the baseplate. The method can further comprise engaging the one or more fins with one or more channels in the resected proximal surface of the tibia to mount the tibial implant on the tibia.

In Example 38, the method of Example 37 can further comprise providing the one or more fins with a porous material to promote bone ingrowth from the channel.

In Example 39, the method of Example 37 the baseplate can comprise a medial side, a lateral side, an anterior bridge portion, and an intercondylar component. The medial side can have at least one of the one or more fins extending from an underside thereof. The lateral side can have at least one of the one or more fins extending from an underside thereof. The anterior bridge portion can connect the medial and lateral sides such that a cut-out is formed between inner surfaces of the medial and lateral sides. The intercondylar component can be attachable to or integral with the baseplate.

In Example 40, the method of Example 39 further comprise engaging the intercondylar component with at least a portion of the retained intercondylar eminence to promote bone ingrowth.

In Example 41, the method of Example 37 the baseplate can comprise only one of a medial side having at least one of the one or more fins extending from an underside thereof or a lateral side having at least one of the one or more fins extending from an underside thereof.

In Example 42, the method of Example 41 can further comprise an intercondylar component attachable to or integral with the baseplate.

In Example 43, the method of claim 42 can further comprise engaging the intercondylar component with at least a portion of the retained intercondylar eminence to promote bone ingrowth.

In Example 44, the system or method of any one or any combination of Examples 1-43 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present tibial prosthesis systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3C is a perspective view of an underside of the tibial baseplate and the intercondylar component of FIG. 3A.

FIG. 4A is an anterior view of a partially resected tibia in accordance with the present application.

FIG. 4B is an anterior view of the partially resected tibia of FIG. 4A with a groove formed in the remaining portion of the intercondylar eminence in accordance with the present application.

DETAILED DESCRIPTION

The present application relates to devices and methods for a tibial prosthesis that can be used in a total knee arthroplasty (TKA) procedure or a unicompartmental knee replacement procedure. An intercondylar component can be attachable to a tibial implant for use with a partially resected tibia in a total knee arthroplasty procedure or a unicompartmental arthroplasty procedure. The partially resected tibia can include at least a portion of the intercondylar eminence and the ACL and/or PCL. The intercondylar component can be configured for engagement with the retained intercondylar eminence when the tibial implant is attached to the resected tibia. The intercondylar component can be formed of a porous structure to promote bone regrowth or ingrowth of the intercondylar eminence or the resected proximal surfaces of the tibia. The present application further describes one or more fins for a tibial prosthesis that can be used in the TKA procedure or the unicompartmental knee replacement procedure. The one or more fins can be adapted to fix the tibial prosthesis to the tibia. In some instances, the fins can be formed of a porous structure to promote bone regrowth or ingrowth of the resected proximal surfaces of the tibia.

Figure 1A:
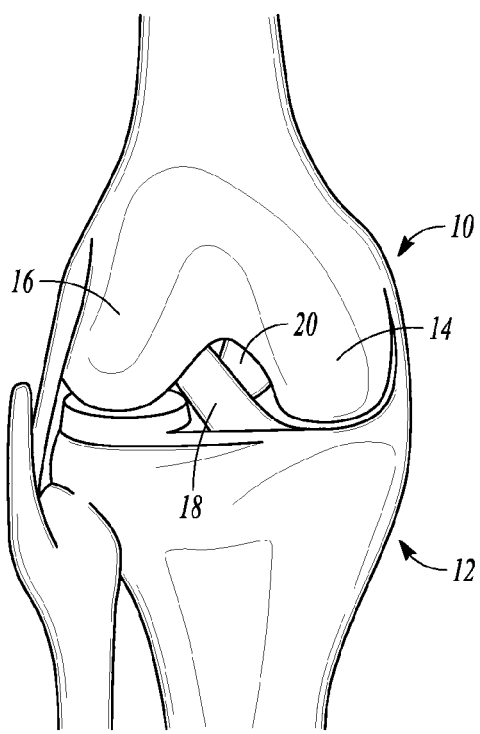
FIG. 1A is an anterior view of a natural femur and tibia.
Figure 1B:
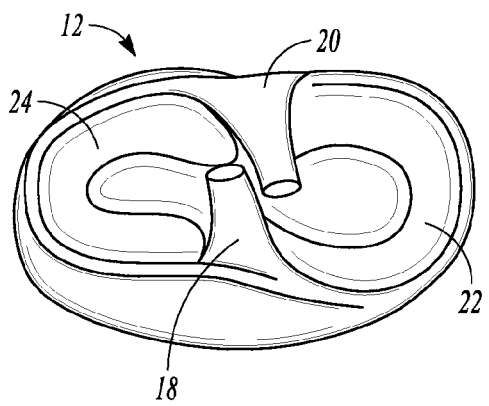
FIG. 1B is a top view of the tibia of FIG. 1A.

FIG. 1A illustrates a natural femur 10 and tibia 12. The femur 10 can include medial 14 and lateral 16 condyles at a distal end of the femur 10. Various ligaments can be attached to the femur 10 and/or the tibia 12. An anterior cruciate ligament (ACL) 18 can extend from an anterior side of the tibia 12 to the femur 10, and a posterior cruciate ligament (PCL) 20 can extend from a posterior side of the tibia 12 to the femur 10. FIG. 1B is a top view of the tibia 12 and further illustrates some of these ligaments as well as a medial meniscus 22 and a lateral meniscus 24 that are located between the tibia 12 and the medial 14 and lateral 16 condyles.

Figure 1C:
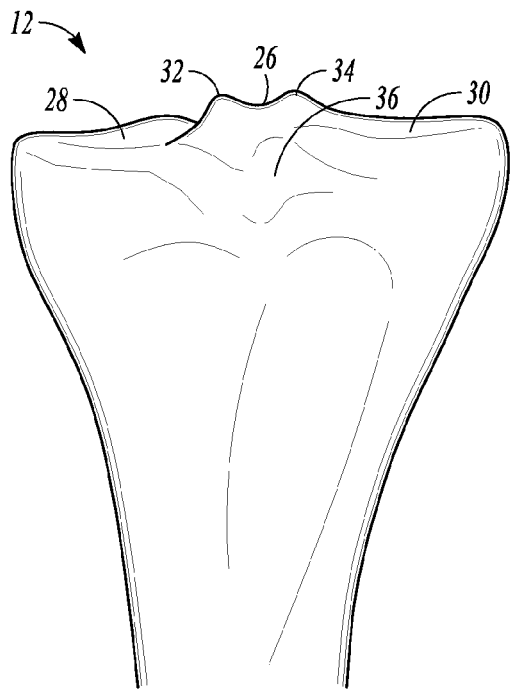
FIG. 1C is a posterior view of the tibia of FIGS. 1A and 1B, with the components shown in FIG. 1B removed.

FIG. 1C illustrates a posterior side view of the tibia 12 with the ligaments and other components shown in FIG. 1B removed. The tibia 12 can include an intercondylar eminence 26, which is a bony elevation or raised area between a medial articular surface 28 and a lateral articular surface 30 at a proximal end of the tibia 12. The intercondylar eminence 26 can include medial 32 and lateral 34 tubercles extending from the intercondylar eminence 26. The ACL 18 and PCL 20 are attached to the tibia 12 at locations anterior and posterior, respectively, to the intercondylar eminence 26. For reference, the PCL 20 is attached to the tibia 12 at a location 36 on a posterior end of the tibia 12.

In a total knee arthroplasty (TKA) procedure, the distal end of the femur 10 and the proximal end of the tibia 12 are resected and replaced with a femoral prosthesis and a tibial prosthesis. As part of performing the resections to the tibia 12, the medial meniscus 22, the lateral meniscus 24 and at least some of the ligaments are removed. Depending on a design of the tibial prosthesis, particularly a design of the tibial baseplate, it is common in a TKA procedure to remove the intercondylar eminence 26 and the ACL 18; in some cases, the PCL 20 is removed. However, it may be advantageous to retain the ACL 18 and/or PCL 20. If the intercondylar eminence 26 is maintained, it can help support the retained ACL 18 and/or PCL 20. Moreover, retaining the intercondylar eminence 26 can be advantageous if a revision procedure is later needed. It can be difficult to remove the original implants, particularly if bone ingrowth has occurred. If the intercondylar eminence 26 or a portion thereof is still present, the surgeon can cut through the retained intercondylar eminence 26 during the revision, which can significantly aid in removing the original implants.

Figure 2:
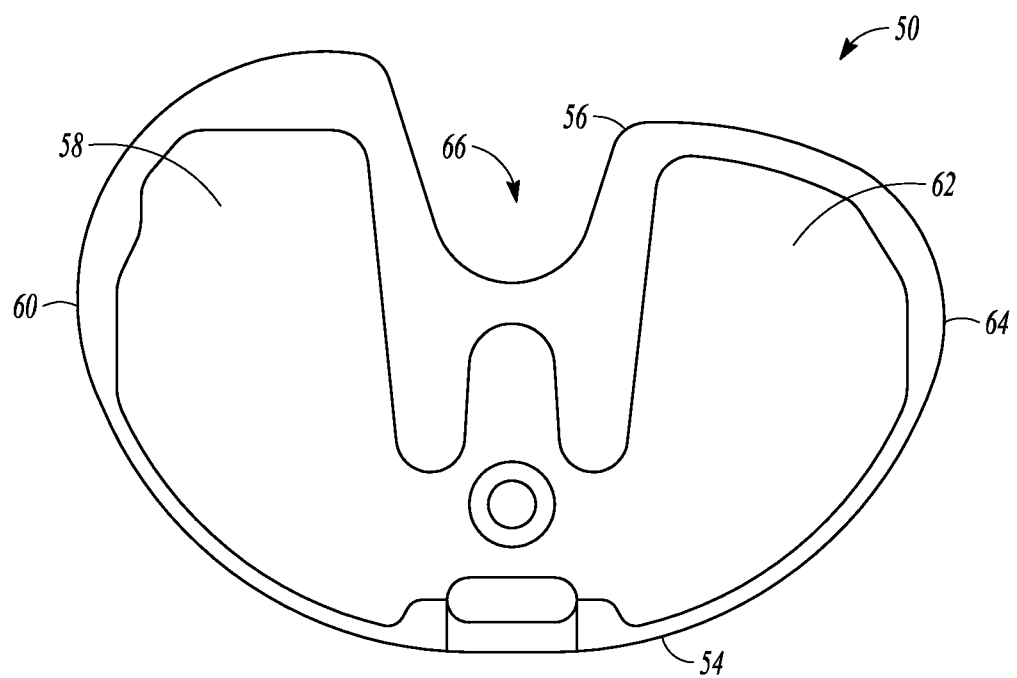
FIG. 2 is a top view of an example of a tibial baseplate.

FIG. 2 shows an example of a tibial baseplate 50 used in a TKA procedure. The tibial baseplate 50 can be placed on a resected surface of a proximal tibia and can be configured to engage with another component of the knee prosthesis, such as a tibial bearing component or insert. The tibial baseplate 50 can include an anterior end 54, a posterior end 56, a medial compartment 58, a medial side 60, a lateral compartment 62, and a lateral side 64. The tibial baseplate 50 can include a PCL cut-out 66 formed at the posterior end 56 between the medial 58 and lateral 62 compartments. This design of the tibial baseplate 50 can accommodate retaining the PCL in a TKA procedure; however, the ACL and intercondylar eminence would typically be sacrificed. In other designs, a tibial baseplate may exclude the PCL cut-out 66, in which case the PCL would also be sacrificed in the procedure.

Figure 3A:
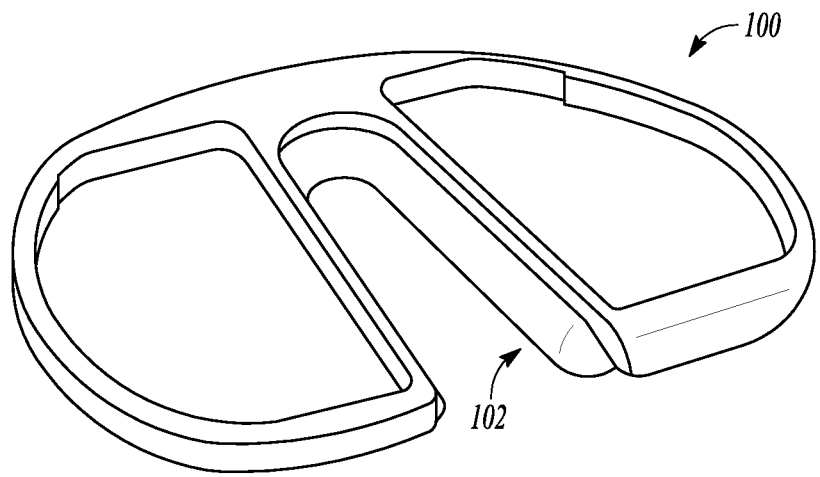
FIG. 3A is a perspective view of an example of a tibial baseplate and an intercondylar component in accordance with the present application.
Figure 3B:
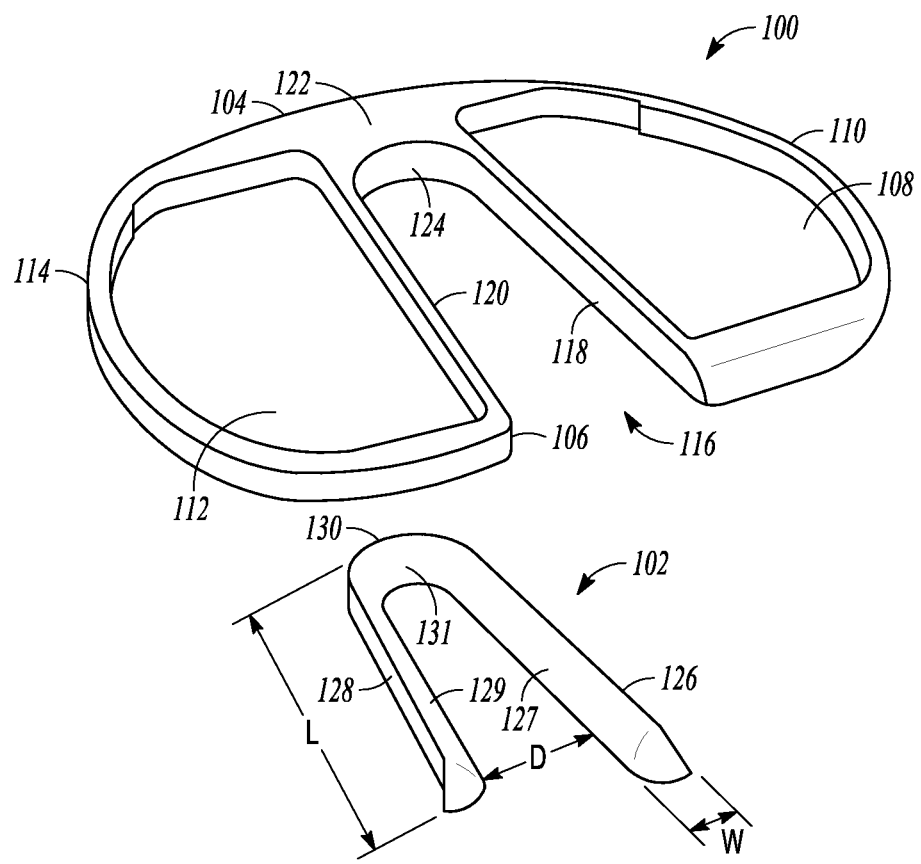
FIG. 3B is a perspective view of the tibial baseplate and the intercondylar component of FIG. 3A separate from one another.

The present application discloses intercondylar components usable with a tibial baseplate in a TKA procedure or a partial knee replacement, and configured for engagement with at least a portion of an intercondylar eminence retained after partially resecting a proximal surface of the tibia. FIG. 3A shows an example of a tibial baseplate 100 and an intercondylar component 102 attached to or integral with the baseplate 100. FIG. 3B shows the tibial baseplate 100 and intercondylar component 102 separate from one another.

The tibial baseplate 100 can be similar in structure to the tibial baseplate 50 of FIG. 2 and can include an anterior end 104, a posterior end 106, a medial compartment 108, a medial side 110, a lateral compartment 112, and a lateral side 114. A notch or cut-out 116 can be formed in the tibial baseplate 100 between an inner surface 118 of the medial compartment 108 and an inner surface 120 of the lateral compartment 112. In an example, the notch or cut-out 116 can be larger and extend further towards the anterior end 104 of the baseplate 100, as compared to the PCL cut-out 66 of the tibial baseplate 50. An anterior bridge portion 122 of the baseplate 100 can be located at the anterior end 104 of the baseplate 100 between the medial 108 and lateral 112 compartments and can include an inner surface 124 having a generally arcuate shape.

The intercondylar component 102 can be configured to attach to or be integral with the inner surfaces 118, 120 and 124 of the tibial baseplate 100 that define the notch or cut-out 116. The intercondylar component 102 can thus have an overall outer shape that generally matches with a shape of the notch or cut-out 116 and can include a medial elongated portion 126 configured to connect to the inner surface 118 of the medial compartment 108, a lateral elongated portion 128 configured to connect to the inner surface 120 of the lateral compartment 112, and an arcuate portion 130 configured to connect to the bridge portion 122 of the baseplate 100. As described further below, an inner shape of the intercondylar component 102, defined by inner surfaces 127, 129 and 131, can generally match with a shape of a remaining portion of the intercondylar eminence of the tibia after the tibia has been resected and prepared to receive the tibial component 100.

The intercondylar component 102 can have an overall length, L and a width, W. The width W can be defined as a spacing between an inner and corresponding outer surface of the component 102. In an example, the width W can be the same for each of the medial and lateral elongated portions 126 and 128 and the arcuate portion 130. In other examples, the width W can be variable among the different portions of the component 102. A distance D can be defined between the inner surfaces 127 and 129 of the medial and lateral elongated portions 126 and 128, respectively. A size and dimensions of a particular intercondylar component 102 can be determined based, in part, on a size of the tibial baseplate 100 or the patient's anatomy, as described below.

In an example, as shown in FIG. 3B, the intercondylar component 102 can be separate from the tibial baseplate 100. The intercondylar component 102 can be formed of a material different than or the same as the tibial baseplate 100. The baseplate 100 can be formed of a biocompatible metal or metal alloy, such as, for example, titanium, a titanium alloy, cobalt chromium, cobalt chromium molybdenum, tantalum, or a tantalum alloy. In an example, the baseplate 100 comprises a Ti-6Al-4V ELI alloy, such as Tivanium® which is available from Zimmer, Inc., of Warsaw, Ind. Tivanium® is a registered trademark of Zimmer, Inc. In an example, all or a portion of the baseplate 100 can be formed of a polymeric material, such as, for example, polyethylene, as described below in reference to FIGS. 5A and 5B. In an example, the intercondylar component 102 can be formed of a metal or metal alloy, including those suitable for use in the baseplate 100, or the intercondylar component 102 can be formed of a porous structure, such as a porous metal described below, to facilitate bone ingrowth or regrowth.

A highly porous metal structure can incorporate one or more of a variety of biocompatible metals. Such structures are particularly suited for contacting bone and soft tissue, and in this regard, can be useful as a bone substitute and as cell and tissue receptive material, for example, by allowing tissue to grow into the porous structure over time to enhance fixation (i.e., osseointegration) between the structure and surrounding bodily structures. According to certain embodiments of the present disclosure, an open porous metal structure may have a porosity as low as 55%, 65%, or 75% or as high as 80%, 85%, or 90%, or within any range defined between any pair of the foregoing values. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other biocompatible metals may also be used in the formation of a highly porous metal structure such as titanium, a titanium alloy, cobalt chromium, cobalt chromium molybdenum, tantalum, a tantalum alloy, niobium, or alloys of tantalum and niobium with one another or with other metals. It is also within the scope of the present disclosure for a porous metal structure to be in the form of a fiber metal pad or a sintered metal layer, such as a Cancellous-Structured Titanium™ (CSTi™) layer. CSTi™ porous layers are manufactured by Zimmer, Inc., of Warsaw, Ind. Cancellous-Structured Titanium™ and CSTi™ are trademarks of Zimmer, Inc.

Generally, a highly porous metal structure will include a large plurality of metallic ligaments defining open voids (i.e., pores) or channels therebetween. The open spaces between the ligaments form a matrix of continuous channels having few or no dead ends, such that growth of soft tissue and/or bone through open porous metal is substantially uninhibited. Thus, the open porous metal may provide a lightweight, strong porous structure which is substantially uniform and consistent in composition, and provides a matrix (e.g., closely resembling the structure of natural cancellous bone) into which soft tissue and bone may grow to provide fixation of the implant to surrounding bodily structures. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

An open porous metal structure may also be fabricated such that it comprises a variety of densities in order to selectively tailor the structure for particular orthopedic applications. In particular, as discussed in the above-incorporated U.S. Pat. No. 5,282,861, an open porous metal structure may be fabricated to virtually any desired density, porosity, and pore size (e.g., pore diameter), and can thus be matched with the surrounding natural tissue in order to provide an improved matrix for tissue ingrowth and mineralization. According to certain embodiments, an open porous metal structure may be fabricated to have a substantially uniform porosity, density, and/or void (pore) size throughout, or to comprise at least one of pore size, porosity, and/or density being varied within the structure. For example, an open porous metal structure may have a different pore size and/or porosity at different regions, layers, and surfaces of the structure. The ability to selectively tailor the structural properties of the open porous metal, for example, enables tailoring of the structure for distributing stress loads throughout the surrounding tissue and promoting specific tissue ingrown within the open porous metal.

In other embodiments, an open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Because the intercondylar component 102 can be formed of a porous structure, like the above-described porous tantalum, the component 102 can promote bone ingrowth of the resected surfaces of the tibia surrounding the component 102 and bone ingrowth of the remaining portion of the intercondylar eminence, as described further below.

FIG. 3C is a bottom view of the tibial baseplate 100 and the intercondylar component 102 in the assembled position. In an example, ends 132 and 134 of the medial 126 and lateral 128 elongated portions, respectively, can extend underneath an underside 136 of the tibial baseplate 100 to secure the intercondylar component 102 to the baseplate 100. In an example, a length of the medial 126 and lateral 128 elongated portions can be such that the medial 126 and lateral 128 elongated portions do not extend to posterior edges 138 and 140 of the medial 108 and lateral 112 compartments. In other examples, the medial 126 and lateral 128 elongated portions can be longer relative to the tibial baseplate 100 and extend to or closer to the posterior edges 138 and 140 of the medial 108 and lateral 112 compartments. The intercondylar component 102 can be attached to the tibial baseplate 100 using known attachment techniques, including, but not limited to, bone cement or other adhesion materials, bonding, or mechanical fixation, such as, for example, screws, a snap fit, and other mechanical features to promote fixation. Bonding of one component to another component, such as component 102 to baseplate 100, is described further below in reference to bonding a porous material to a metal component.

FIG. 4A is a perspective view of a tibia 150 having a partially resected proximal surface 151. After the menisci and ligaments have been removed, the tibia 150 would look similar to the tibia 12 as shown in FIG. 1C. Additional steps can then be performed to prepare the tibia 150 for attachment of the tibial baseplate 100 and intercondylar component 102 to the tibia 150. Separate resections can be performed on a medial articular surface and a lateral articular surface of the tibia (see surfaces 28 and 30 of FIG. 1C)—to create medial 152 and lateral 154 resected surfaces. These resections may result in removal of some of the intercondylar eminence 156 near the medial and lateral compartments of the tibia 150. However, a goal of the TKA procedure as described herein is to maintain a majority of the intercondylar eminence 156. An additional resection can be performed on an anterior side 158 of the tibia 150 between the medial and lateral compartments to create anterior resected surface 160. The remaining portion of the intercondylar eminence 156 includes side walls 162 that form an exterior surface of the remaining portion of the intercondylar eminence 156.

Figure 4C:
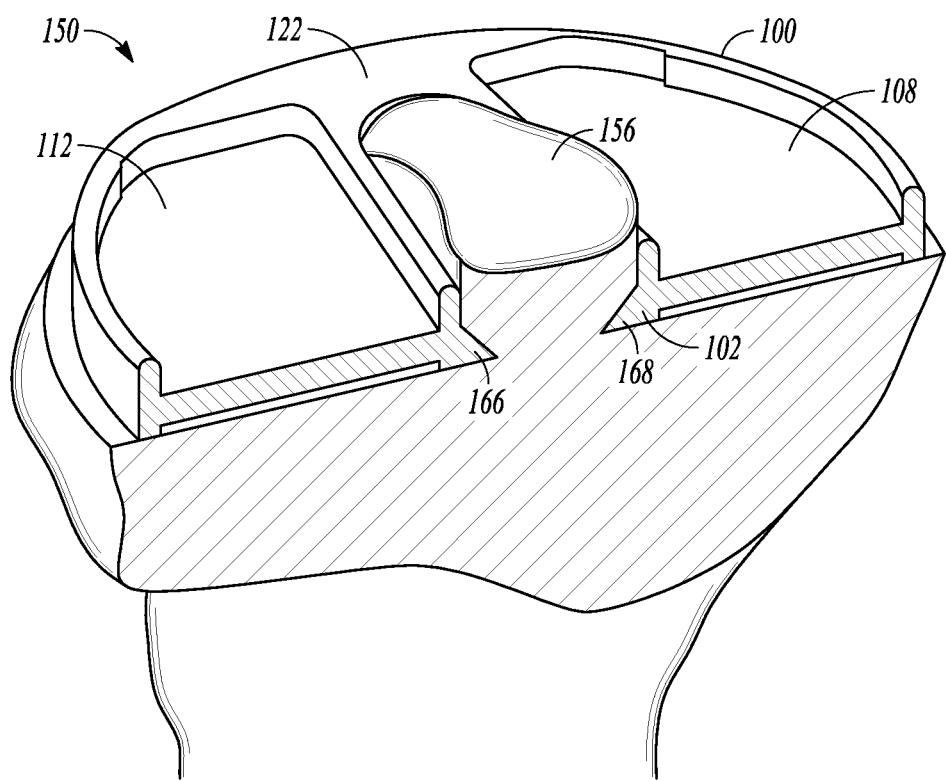
FIG. 4C is a cross-sectional view extending through the partially resected tibia of FIGS. 4A and 4B and the tibial baseplate of FIG. 3A, the tibial baseplate attached to the tibia in accordance with the present application.

FIG. 4B shows the tibia 150 of FIG. 4A after a groove 164 has been formed in the side walls 162 of the remaining portion of the intercondylar eminence 156. Engagement of the groove 164 with the intercondylar component 102 is described below in reference to FIG. 4C. In other examples, formation of the groove 164 can be excluded from these steps of preparing the tibia 150 for attachment of the tibial baseplate 100 and intercondylar component 102.

FIG. 4C shows a cross-section of the tibial baseplate 100 and intercondylar component 102 of FIGS. 3A-3C as well as a cross-section of the partially resected tibia 150. The tibial baseplate 100 and intercondylar component 102 are attached to partially resected tibia 150. (The tibia 150 has been rotated approximately 180 degrees in FIG. 4C relative to its position in FIG. 4B.) The medial compartment 108 of the tibial baseplate 100 can attach to the medial resected surface 152, the lateral compartment 112 can attach to the lateral resected surface 154, and the anterior bridge portion 122 can attach to the anterior resected surface 160. A size and shape of the remaining portion of the intercondylar eminence 156 can correspond to the inner shape of the intercondylar component 102 such that the intercondylar component 102 can engage with the side walls 162 of the intercondylar eminence 156. In an example, the intercondylar component 102 can be pressed into the groove 164 formed in the side walls 162 to form a press fit, as indicated at locations 166 and 168 in FIG. 4C.

The intercondylar component 102 can be designed for engagement with the remaining portion of the intercondylar eminence 156. In an example in which the intercondylar component 102 is formed of a porous material, the intercondylar component 102 can help promote bone growth of the intercondylar eminence 156 and bone growth of the resected tibial surfaces that the intercondylar component 102 and the baseplate 100 are attached to. This bone growth can help secure the baseplate 100 to the tibia 150 and in some cases, can eliminate or minimize a need for bone cement or other fixation techniques.

Differently-sized intercondylar components can be made available to the surgeon or other user which are similar to the intercondylar component 102 and increase in size to correspond to the various sizes of tibial baseplates. The length L of the intercondylar component 102 (see FIG. 3B) can vary depending on a size and configuration of the tibial baseplate it is to be used with. The width W of the intercondylar component 102 (see FIG. 3B) can also vary based on a size and design of the tibial baseplate or a specific structure of a patient's tibia, including the intercondylar eminence 156. The intercondylar component 102 having a reduced width or an increased width, based, in part, on an overall size of the patient's tibia and the dimensions of the remaining portion of the intercondylar eminence. In an example, as part of a procedure to partially resect the tibia, in some instances more of a patient's intercondylar eminence may be removed relative to a procedure on another patient and thus the dimensions of the intercondylar component selected can depend on each patient's anatomy and the particular dimensions of the remaining portion of the intercondylar eminence.

Various intercondylar components having a general design similar to the intercondylar component 102 can be configured for use with different designs of a tibial baseplate. It is recognized that other baseplate designs in addition to the baseplate 100 shown in FIGS. 3A-3C can be used in a TKA procedure and the intercondylar component as described herein can be modified to accommodate a particular tibial baseplate design.

Figure 5A:
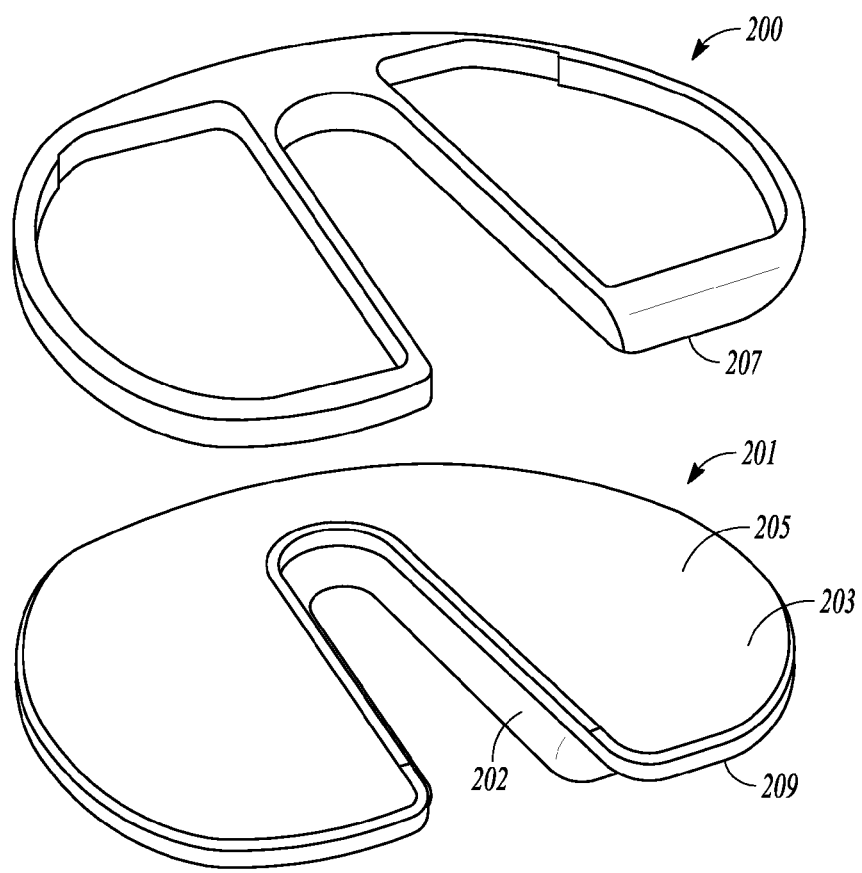
FIG. 5A is a perspective view of an example of a tibial baseplate and a tibial component, including a plate and an intercondylar component, in accordance with the present application.
Figure 5B:
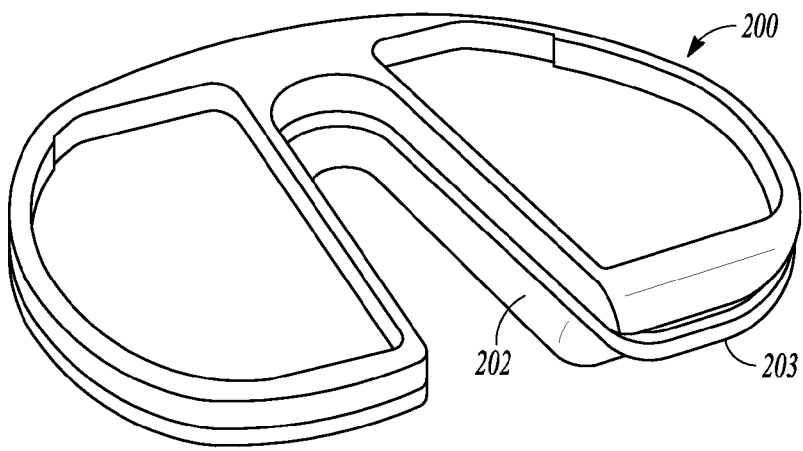
FIG. 5B is a perspective view of the tibial baseplate and the tibial component of FIG. 5B attached together in accordance with the present application.

FIG. 5A shows an example of a tibial baseplate 200 and a tibial component 201 including an intercondylar component 202. The intercondylar component 202 can be similar to the intercondylar component 102 described above and shown in FIGS. 3A-3C, but can be integrally formed with a plate 203 such that the plate 203 and the intercondylar component 202 constitute the tibial component 201. The plate 203 and the intercondylar component 202 can be attached to the tibial baseplate 200 as shown in FIG. 5B. Specifically, a superior surface 205 of the plate 203 can be attachable to an underside or inferior surface 207 of the tibial baseplate 200. Attachment of the plate 203 to the baseplate 200 is described below.

As described above in reference to the intercondylar component 102 of FIGS. 3A-3C, the intercondylar component 202 can be formed of a porous structure that can promote bone growth. All or some of the plate 203 can be formed of a porous structure, including the porous materials described above in reference to the intercondylar component 102. An inferior surface 209 of the plate 203 can be attached to the resected surfaces of the tibia. The intercondylar component 202 can engage with a remaining portion of the intercondylar eminence of the tibia as described above in reference to the intercondylar component 102 and provide similar benefits.

The plate 203, having the inferior (or bone contacting) surface 209 that can be formed of a porous material, can promote bone ingrowth and promote secure and stable fixation of the tibial component 201 and thus the tibial baseplate 200 to the resected tibia. This can eliminate or minimize a need for bone cement which has traditionally been used for fixation of tibial implants to the resected bone, although it is recognized that bone cement can still be used with the tibial implants described herein. Eliminating bone cement can facilitate bone ingrowth by allowing bone to interdigitate with the bone contacting surface 209 of the tibial component 201. This can provide stronger and more secure fixation than can sometimes be achieved between solid metal, or other similar materials, and bone. The tibial baseplate 200 can be formed of a different material than the tibial component 201, such as a material conducive to articulation or engagement with another part of the tibial prosthesis, such as, for example, a bearing component. With the inclusion of plate 203, the benefits of the porous material can be achieved for the bone contacting surfaces, while the tibial baseplate 200 can be formed of a material(s) suitable for articulation or engagement with another prosthesis component.

The baseplate 200 can be formed of a biocompatible metal or metal alloy, including those listed herein. The baseplate 200 can be formed of a polymeric material such as polyethylene and, in particular ultra high molecular weight polyethylene (UHMWPE). In an example, the baseplate 200 can be formed from a crosslinked ultrahigh molecular weight polyethylene blend stabilized with Vitamin E, such as disclosed in U.S. Pat. No. 7,846,376. The tibial component 201 and the baseplate 200 can be bonded together. In an example, the polymeric material that forms the baseplate 200 can be molded at least partially within the porous structure forming component 201 to form a unified construct. In addition to the baseplate 200, it is recognized that other components described herein can be formed of a polymeric material, such as polyethylene, and can be bonded with other components formed from the porous structures described herein.

The tibial component 201 can be attached to the underside 207 of the tibial baseplate 200 using known techniques. In an example, the superior surface 205 of the plate 203 can be attached to the underside 207 of the baseplate 200 using known techniques for bonding or attaching a porous structure, such as tantalum, to the baseplate 100, which can be formed of a metal or metal alloy. Reference is made to U.S. Pat. No. 7,918,382, entitled "METHOD FOR ATTACHING A POROUS METAL LAYER TO A METAL SUBSTRATE", and directed to a method for attaching a porous metal structure to a metal substrate for forming orthopedic implants; and U.S. Pat. No. 8,608,049, entitled "METHOD FOR BONDING A TANTALUM STRUCTURE TO A COBALT-ALLOY SUBSTRATE", and directed to a method for bonding a porous tantalum structure to a substrate comprising cobalt or a cobalt-chromium alloy. Reference is also made to U.S. Published Application No. 2012/0125896, entitled "RESISTANCE WELDING A POROUS METAL LAYER TO A METAL SUBSTRATE", and directed to an apparatus and method for manufacturing an orthopedic prosthesis by resistance welding a porous metal layer to a metal substrate of the orthopedic prosthesis.

Figure 6A:
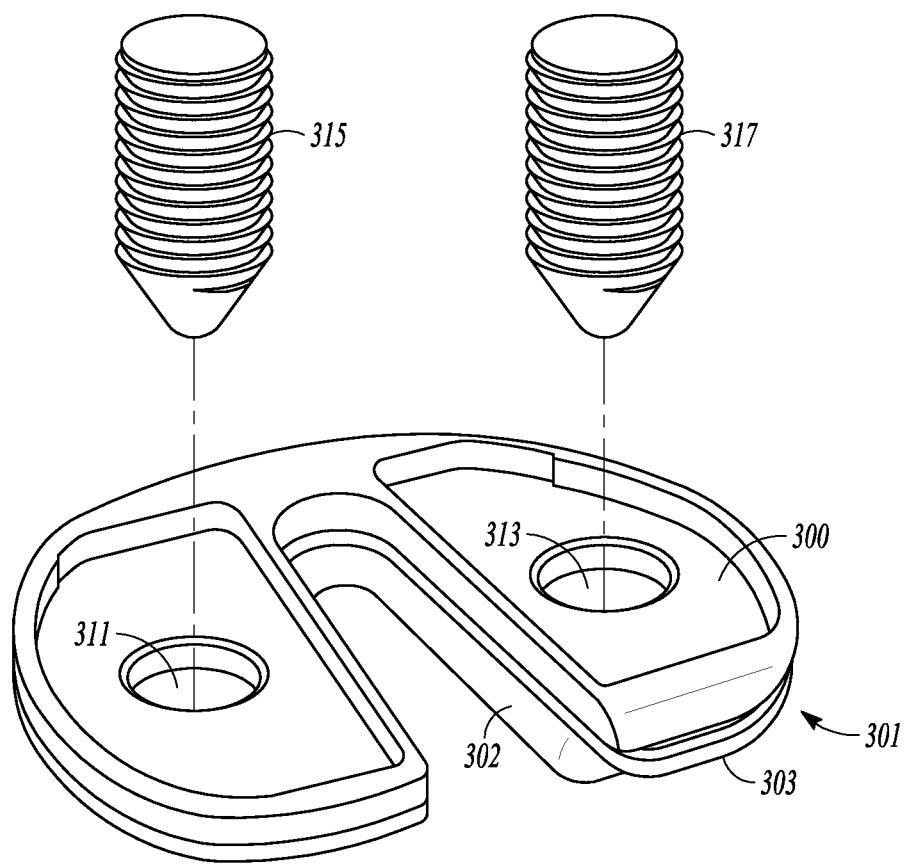
FIG. 6A is a perspective view of an example of a tibial baseplate, a tibial component, and bone screws for attaching the tibial baseplate and tibial component to a resected tibia, in accordance with the present application.

As stated above, bone cement can traditionally be used to secure a tibial baseplate or other tibial component to a resected surface of the tibia. In addition to or as an alternative to bone cement, fasteners can be used to secure the tibial baseplate to the resected surface. FIG. 6A shows an example of a tibial baseplate 300, similar to the tibial baseplate 200, and having a tibial component 301, similar to the tibial component 201 and including an intercondylar component 302 and a plate 303, attached thereto. The tibial baseplate 300 and the plate 303 can each include one or more openings 311 and 313 configured to receive bone screws 315 and 317.

Figure 6B:
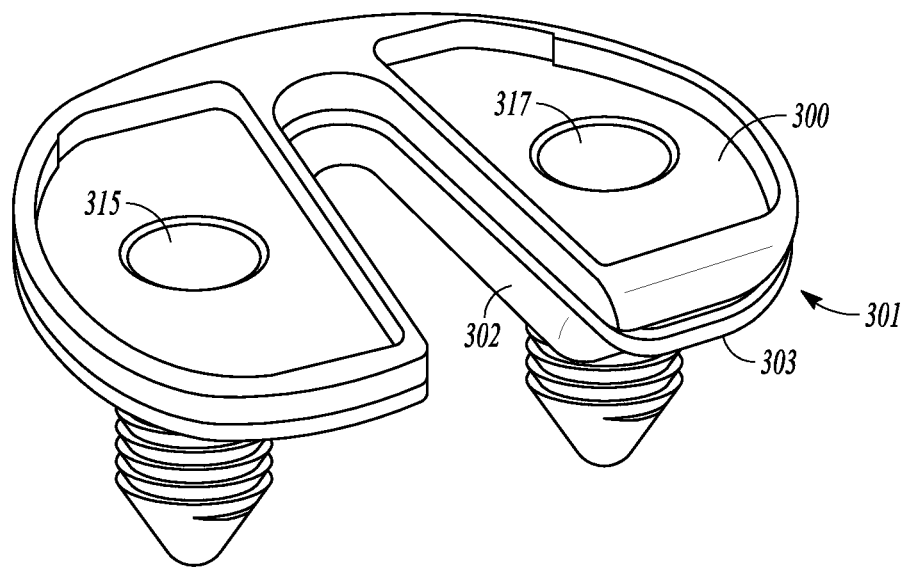
FIG. 6B is a perspective of the tibial baseplate and the tibial component of FIG. 6A with the bone screws inserted into openings in the tibial baseplate and tibial component.

As shown in FIG. 6B, the screws 315 and 317 can be installed in the openings 311 and 313, respectively, after the baseplate 300 is implanted on a partially resected tibia. The screws 315 and 317 can be implanted after the intercondylar component 302 is pressed into position for engagement with a remaining portion of the intercondylar eminence. Although two openings 311 and 313 and two bone screws 315 and 317 are shown in FIGS. 6A and 6B, it is recognized that more or less than two screws can be used. In an example, all or a portion of the bone screws 315 and 317 can be formed of a porous structure, such as a porous tantalum structure described above, or of a biocompatible metal or metal alloy, including the examples provided above. It is recognized that bone screws 315 or 317, or similar fasteners, are not required for securing the baseplate 300 to the tibia.

The bone screws 315 and 317 are shown in FIGS. 6A-6B for use with a tibial baseplate 300 and a tibial component 301, including a plate 303, which is similar to the design of the tibial baseplate 200 and the tibial component 201 of FIGS. 5A and 5B. It is recognized that bone screws or other fasteners can optionally be used with the design shown in FIGS. 3A-3C in which the intercondylar component 102 attaches directly to the tibial baseplate 100 and an extra plate integral with the intercondylar component 102 is excluded.

Other types of fasteners or fixation features can also be used, as an alternative to the bone screws shown in FIGS. 6A and 6B, for securing the tibial baseplate 300 and the tibial component 301 to the resected tibia.

The tibial implants described herein, which include an intercondylar component, can be configured for use in a total knee replacement or TKA procedure as described above (both the medial and lateral compartments of the tibia are resected and prepared to receive a tibial implant), but are also usable in a partial knee replacement. In a unicompartmental knee arthroplasty procedure, one compartment of the knee is typically repaired and replaced with an implant, while retaining the other compartment as well as the ligaments and the intercondylar eminence.

Figure 7A:
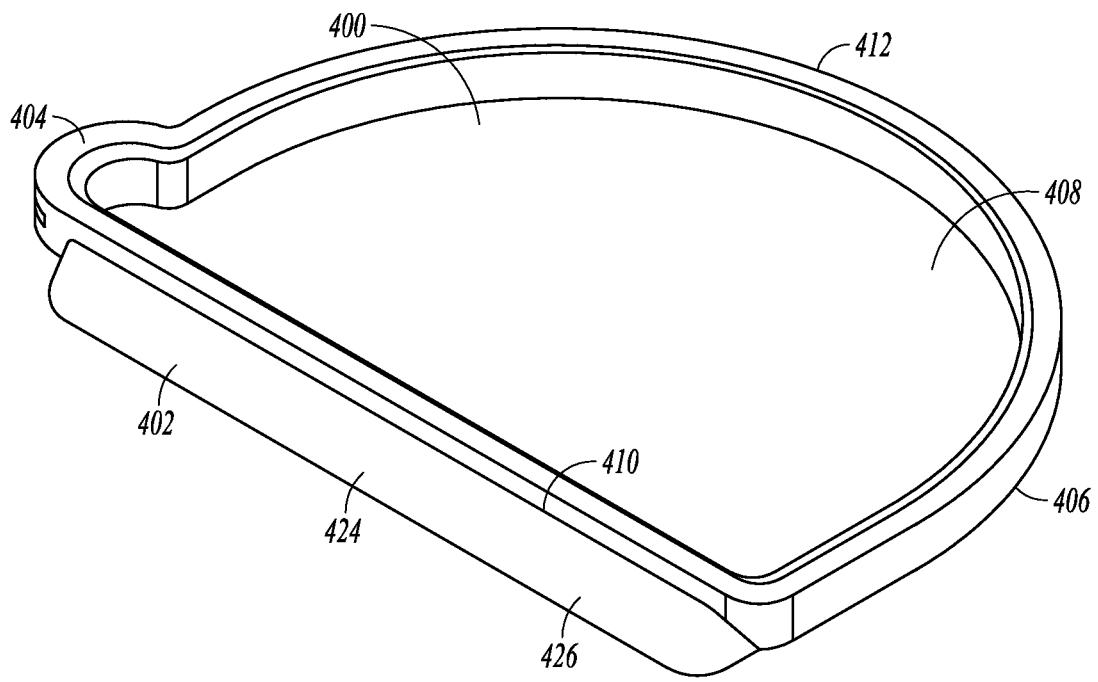
FIG. 7A is a perspective view of a tibial baseplate and an intercondylar component for use in a unicompartmental knee arthroplasty, in accordance with the present application.
Figure 7B:
FIG. 7B is a side view of the tibial baseplate and intercondylar component of FIG. 7A.

FIG. 7A shows an example of a tibial baseplate 400 and an intercondylar component 402 attached thereto, and configured for use in a unicompartmental knee arthroplasty. The tibial baseplate 400 can include an anterior end 404, a posterior end 406, a compartment 408, an inner edge 410 and an outer edge 412. An underside of the tibial baseplate 400 can be configured to attached to a resected surface of the tibia, either on a medial or a lateral side. The baseplate 400 can be shaped such that the compartment 408 generally matches with the medial or lateral side, depending on a right or left knee. The intercondylar component 402 can include an elongated portion 424 configured to engage with the inner edge 410 of the baseplate 400 when the intercondylar component 402 is attached to the baseplate 400. A surface 426 of the elongated portion 424 can be configured to engage with a remaining portion of the intercondylar eminence of the tibia after the tibia has been resected on either a lateral or medial side. FIG. 7B is a side view of the tibial baseplate 400 and the intercondylar component 402 of FIG. 7A and shows the inner edge 410 of the tibial baseplate with the intercondylar component 402 attached thereto and extending underneath an underside of the tibial baseplate 400.

In a unicompartmental procedure, the intercondylar component 402 can help to facilitate bone ingrowth underneath the tibial baseplate 400 and bone ingrowth of the remaining portion of the intercondylar eminence. In an example, the tibial baseplate 400 can be formed of a metal or metal alloy, as described above, and the intercondylar component 402 can be a porous structure, such as porous tantalum. As similarly described above in reference to the tibial baseplate 200, the baseplate 400 or a portion thereof can be formed of a polymeric material, such as ultra-high molecular weight polyethylene.

In an example, the tibial baseplate 400 can include one or more openings that can be configured to receive one or more bone screws, or other fasteners, as similarly described above in reference to FIGS. 6A and 6B, for further securing the tibial baseplate 400 and the intercondylar component 402 to the resected tibia.

In an example, an intercondylar component similar to the intercondylar component 402 can be integral with a plate 403 to form a tibial implant which can attach to an underside of the tibial baseplate 400, as similarly described above in reference to FIGS. 5A and 5B. The plate 403 can similarly be formed of a porous structure, as described above.

In some instances, a bi-unicompartmental knee arthroplasty procedure can be performed in which a tibial baseplate and an intercondylar component similar to those shown in FIG. 7A can be implanted in both a medial compartment and a lateral compartment of a resected tibia. All or a portion of the intercondylar eminence can be retained and each intercondylar component can engage with the retained portion of the intercondylar eminence to promote bone ingrowth on either side of the intercondylar component.

The present application includes a method of performing a knee arthroplasty for total knee replacement or unicompartmental knee replacement. The method can include partially resecting a proximal surface of a tibia, while retaining at least a portion of an intercondylar eminence of the tibia and at least one of the ACL and PCL. A tibial implant can be attached to the resected proximal surface of the tibia and the tibial implant can include a baseplate having an inferior surface configured to contact the resected proximal surface of the tibia and a superior surface configured to articulate or engage with another component of the knee prosthesis or a condyle or a natural femur. The tibial implant can include an intercondylar component attachable to the baseplate, and the method can include engaging the intercondylar component with at least a portion of the retained intercondylar eminence to promote bone ingrowth. The method can further include, after attaching the tibial implant to the resected surface of the tibia, inserting one or more fasteners through one or more openings in the tibial implant to secure the tibial implant to the tibia.

In an example, the tibial implant can be configured for total knee replacement and can include a medial compartment, a lateral compartment and an anterior bridge portion connecting the two compartments such that a cut-out is formed between the medial and lateral compartments. The intercondylar component can be configured such that the outer surfaces of the intercondylar component are sized and shaped to attach to the inner surfaces of the tibial baseplate that define the cut-out and the inner surfaces of the intercondylar component are configured to contact a remaining portion of the intercondylar eminence of the resected tibia. In an example, the intercondylar component can be part of a tibial implant that includes a plate that attaches to an underside of the tibial implant.

In an example, the tibial baseplate can be configured for unicompartmental or bi-unicompartmental knee replacement and the intercondylar component can be configured to attach to an inner edge of the tibial baseplate. The intercondylar component can be directly attached to the tibial baseplate or integral with a plate that attaches to an underside of the tibial baseplate.

The step in the method recited above of engaging the intercondylar component with a remaining portion of the intercondylar eminence can include forming a press fit between the intercondylar component and the remaining portion of the intercondylar eminence. The method can include forming a groove in side walls of the remaining portion of the intercondylar eminence to facilitate the press fit of the intercondylar component with the intercondylar eminence.

Figure 8:
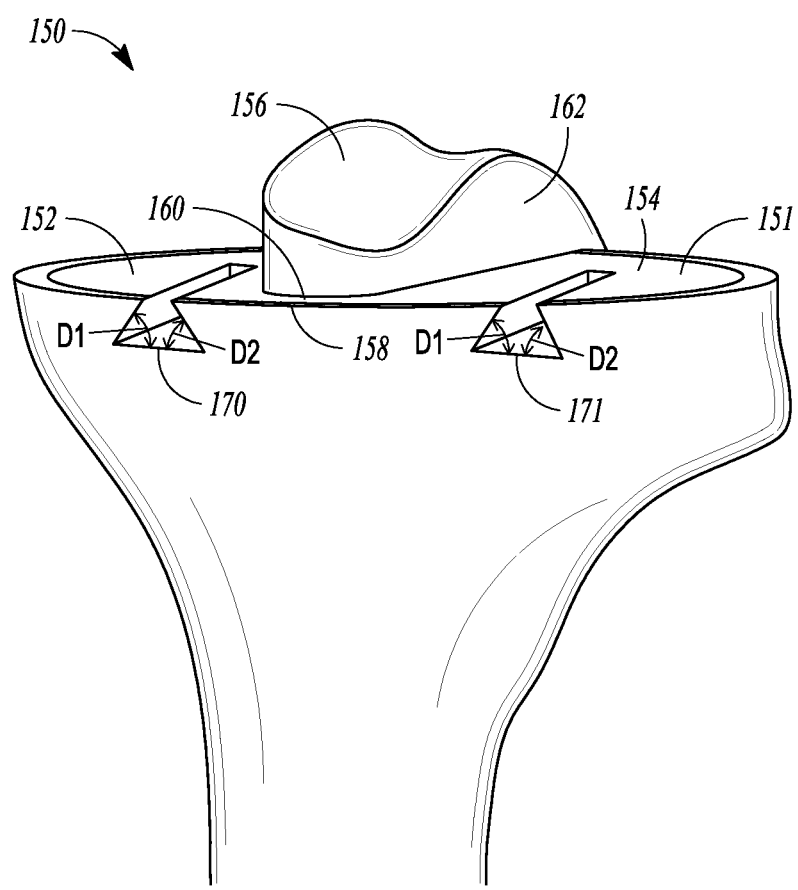
FIG. 8 is an anterior view of a partially resected tibia in accordance with the present application with first and second channels formed in the tibia to either side of the intercondylar eminence.

FIG. 8 is a perspective view of the tibia 150 of FIG. 4A having partially resected proximal surface 151. Additional steps can be performed to prepare the tibia 150 for attachment of the tibial baseplate to the tibia 150 via one or more fins on the tibial baseplate (discussed subsequently).

As illustrated in FIG. 8, a first channel 170 and a second channel 171 can be formed in the tibia 150 and communicate with the medial 152 and lateral 154 resected surfaces, respectively. The first and second channels 170 and 171 can be open to the anterior side 158 of the tibia 150 and extend generally toward the posterior side. In some cases, the first and second channels 170 and 171 can extend through to be open on the posterior side of the tibia 150. In other cases, one or both of the first and second channels 170 and 171 can terminate prior to reaching the posterior side of the tibia 150. The first and second channels 170 and 171 can be formed using known surgical instruments such as, for example, a burr and/or mill. The channel(s) 170 or 171 can be adapted as dovetail slots to receive the fin(s) therein to affix the baseplate to the tibia 150 against forces such as a lift off moment and/or a rotation in the coronal plane. In some instances, the walls of the channel(s) can have acute angles D1 and D2 relative to one another such that a proximal portion of the channel is narrower than a distal portion. Thus, in some examples the channels 170 and 171 can comprise dovetail slots. Various channel configurations (cross-sectional shapes, lengths, etc.) that correspond to the shape of the fins on the tibial baseplate are contemplated in order to facilitate mounting of the baseplate on the tibia 150.

Figure 9:
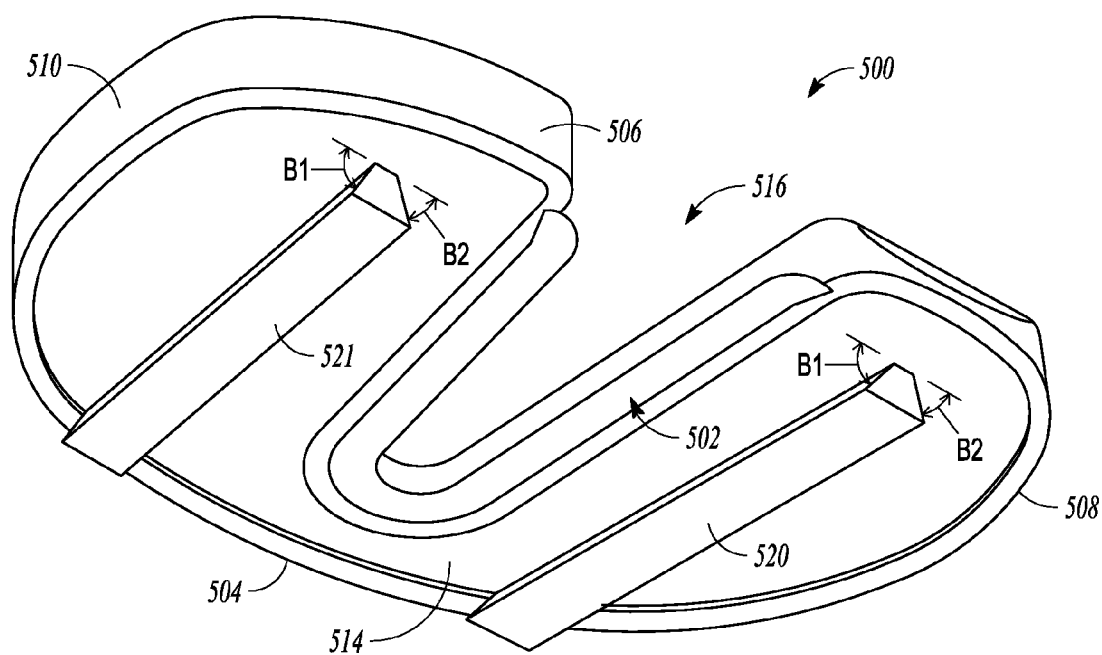
FIG. 9 is a perspective view of an underside of an example of a tibial baseplate having first and second fins in accordance with the present application.

FIG. 9 shows a bottom perspective view of an example of a tibial baseplate 500 used in the TKA procedure. As with the other examples previously described, the tibial baseplate 500 can be placed on a resected surface of a proximal tibia and can be configured to engage with another component of the knee prosthesis, such as a tibial bearing component or insert. The tibial baseplate 500 can include an anterior end 504, a posterior end 506, a medial compartment 508, and a lateral compartment 510. The tibial baseplate 500 can include a PCL cut-out 516 formed at the posterior end 506 between the medial 508 and lateral 510 compartments. As previously discussed, an intercondylar component 502 can be used with the tibial baseplate 500 as illustrated. The tibial baseplate 500 can include a first fin 520 and a second fin 521, which can be integral with or connect to an underside or inferior surface 514 of the tibial baseplate 500.

The first fin 520 and the second fin 521 can extend from the anterior end 504 toward the posterior end 506 of the tibial baseplate 500. In the example as shown in FIG. 9, the first and second fins 520 and 521 can terminate prior to the posterior end 506. In other examples, one or both of the first fin 520 and the second fin 521 can extend to the posterior end 506. The first fin 520 can be disposed along the medial compartment 508 while the second fin 521 can be disposed along the lateral compartment 512. As illustrated the first fin 520 can be spaced from the second fin 521 and extends generally parallel therewith. The first fin 520 can be configured with generally a same shape and size as the second fin 521. However, in other examples the first fin 520 may differ in shape and/or size from the second fin 521. In the example shown in FIG. 9, the side surfaces of the first and second fins 520 and 521 can be at an acute angle B1 and B2 to an inferior (underside) surface giving each of the first fin 520 and the second fin 521 a generally trapezoidal cross-sectional shape. It is recognized that various other configurations for the fins 520 or 521 are contemplated and can be used, but are not specifically discussed herein.

The construction of the tibial baseplate 500 has been discussed previously with regard to other examples above, and therefore, will not be further addressed in detail. In some examples, the first and second fins 520 and 521 can be formed as part of the tibial baseplate 500. Thus, the tibial baseplate 500 and the first and second fins 520 and 521 can be integrally formed. The first and second fins 520 and 521 can be formed of a material different than or the same as the tibial baseplate 500 (e.g., a biocompatible metal or metal alloy). In other examples, the first fin 520 and the second fin 521 can be formed separately from the tibial baseplate 500 and subsequently affixed thereto. The first and second fins 520 and 521 (and a porous substrate if utilized) can be attached to the tibial baseplate 500 using known attachment techniques, including, but not limited to, bone cement or other adhesion materials, bonding, or mechanical fixation, such as, for example, screws, a snap fit, and other mechanical features to promote fixation. In some examples, the first and second fins 520 and 521 can comprise a porous structure, such as the porous metals (e.g., Trabecular Metal™) previously discussed in reference to the examples provided.

Because the first and second fins 520 and 521 can be formed of a porous structure the first and second fins 520 and 521 can promote bone ingrowth of the resected surfaces of the tibia surrounding the first and second fins 520 and 521 in order to better affix the tibial baseplate 500 to the tibia.

Figure 10:
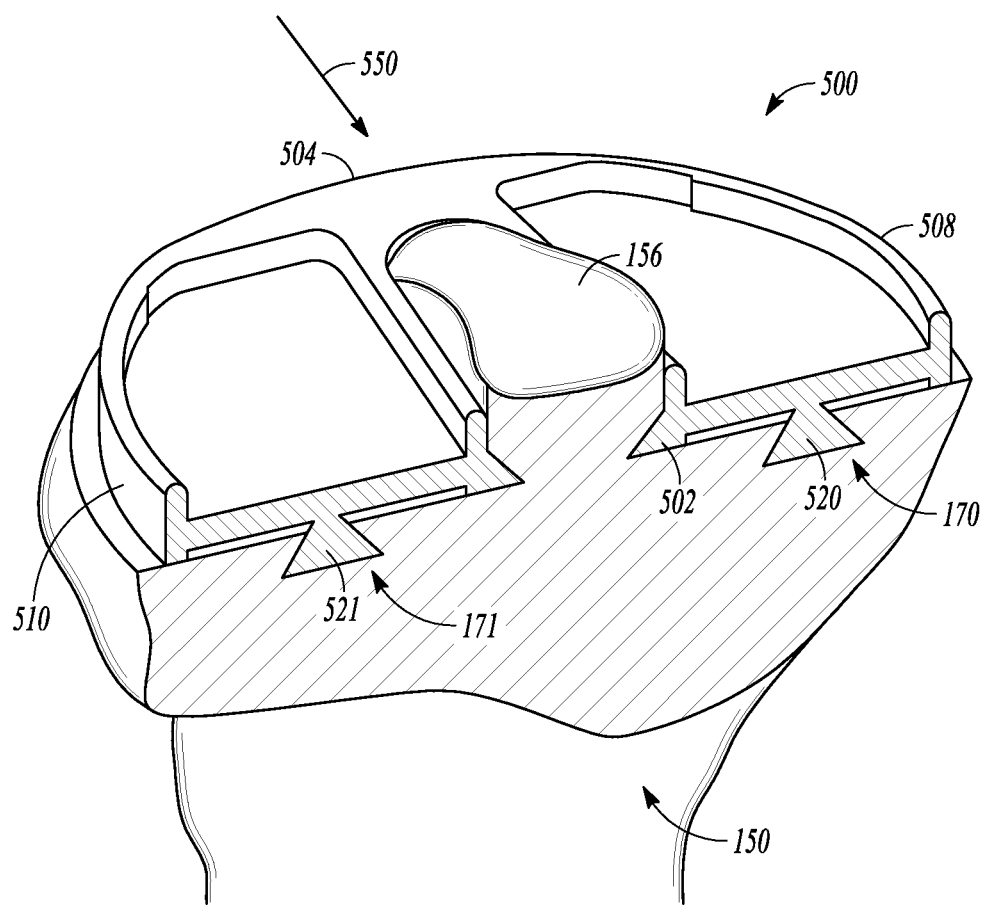
FIG. 10 is a cross-sectional view extending through the partially resected tibia of FIG. 8 and the tibial baseplate with fins of FIG. 9 in accordance with the present application.

FIG. 10 shows a cross-section of the tibial baseplate 500 and tibia 150. The tibial baseplate 500 includes the first and second fins 520 and 521, the intercondylar component 502, and is mounted to the tibia 150. The tibia 150 has been rotated approximately 180 degrees in FIG. 10 relative to its position in FIG. 8. The medial compartment 508 of the tibial baseplate 500 can attach to the medial resected surface 152, the lateral compartment 510 can attach to the lateral resected surface 154, and an anterior bridge portion 522 can attach to the anterior resected surface 160. A size and shape of the remaining portion of the intercondylar eminence 156 can correspond to the inner shape of the intercondylar component 502 such that the intercondylar component 502 can engage with the side walls 162 of the intercondylar eminence 156. Similarly, the first and second fins 520 and 521 can be received in and engage with the side walls of the first and second channels 170 and 171, respectively. In an example, the intercondylar component 502 and first and second fins 520 and 521 can be press fit into their respective mating features. With respect to the first and second fins 520 and 521, the channels 170 and 171 can be adapted to form a press fit or similar connection. In instances where the press fit is used for the fins 520, 521 and channels 170, 171, the tibial baseplate 500 can be mounted onto the tibia 150 (and the fins 520, 521 disposed in the channels 170, 171) by moving the tibial baseplate 500 from an anterior to posterior direction as indicated by arrow 550. The mounting technique allows the fins 520, 521 to track within the channels 170, 171 from an anterior to posterior direction. The mounting technique allows for a smaller incision window (as opposed to a posterior window and insertion) to provide access to the anatomy being reconstructed. Although discussed in reference to a press fit engagement, the intercondylar component 502 and the first and second fins 520 and 521 can be mounted using other known methods (e.g., deposition, adhesives, etc.).

The first and second fins 520 and 521 as wells as the intercondylar component 102 can be designed for engagement with the remaining portions of the tibia 150. In an example in which the intercondylar component 502 and the first and second fins 520 and 521 are formed of a porous material, these features can help promote bone growth of the resected tibial surfaces that these features are attached to. This bone growth can help secure the baseplate 500 to the tibia 150 and in some cases, can eliminate or minimize a need for bone cement or other fixation techniques.

Figure 11:
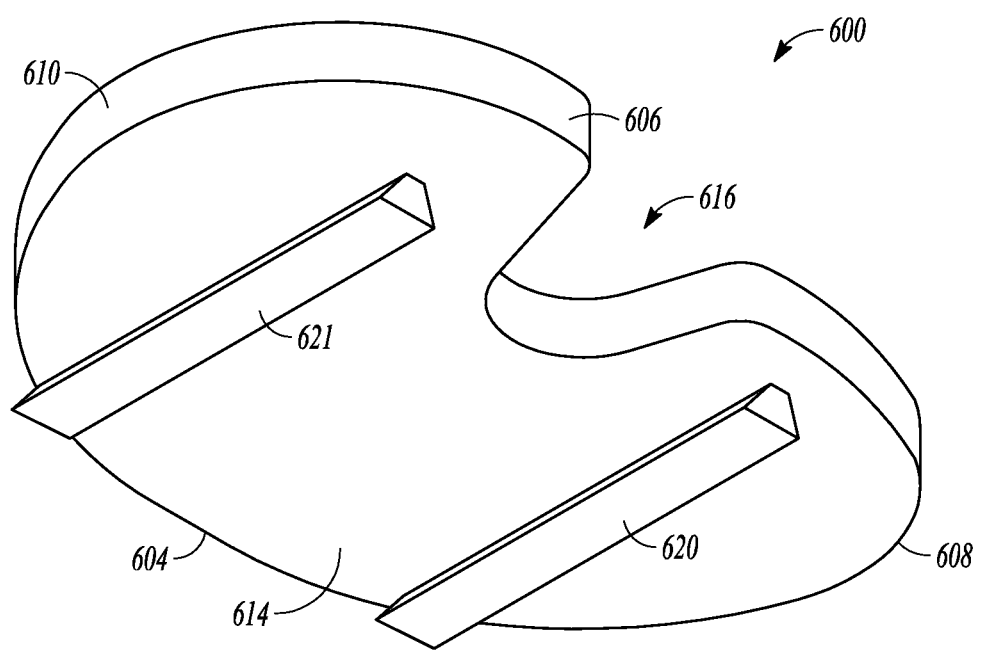
FIG. 11 is a perspective view of an underside of an example of a tibial baseplate having first and second fins in accordance with the present application.

FIG. 11 shows another example of a tibial baseplate 600 used in the TKA procedure. The design of the tibial baseplate 600 can accommodate retaining the PCL in a TKA procedure; however, the ACL and intercondylar eminence could be sacrificed. In other designs, a tibial baseplate may exclude the PCL cut-out 616, in which case the PCL would also be sacrificed in the procedure.

As with the other examples previously described, the tibial baseplate 600 can be placed on a resected surface of a proximal tibia and can be configured to engage with another component of the knee prosthesis, such as a tibial bearing component or insert. The tibial baseplate 600 can include an anterior end 604, a posterior end 606, a medial compartment 608, and a lateral compartment 610. The tibial baseplate 600 can include a PCL cut-out 616 formed at the posterior end 606 between the medial 608 and lateral 610 compartments. A first fin 620 and a second fin 621 can connect to or be integral with an inferior surface 614 of the tibial baseplate 600.

The construction and arrangement of the first and second fins 620 and 621 can be similar to the first and second fins 520 and 521 of FIGS. 9 and 10, and therefore, will not be discussed in great detail. FIG. 11 illustrates that fins can be utilized with designs of the tibial baseplate (e.g., tibial baseplate 600) that do not utilize an intercondylar component. It is further recognized that other baseplate designs can be used in a TKA procedure and the fins as described herein can be modified to accommodate a particular tibial baseplate design.

Figure 12A:
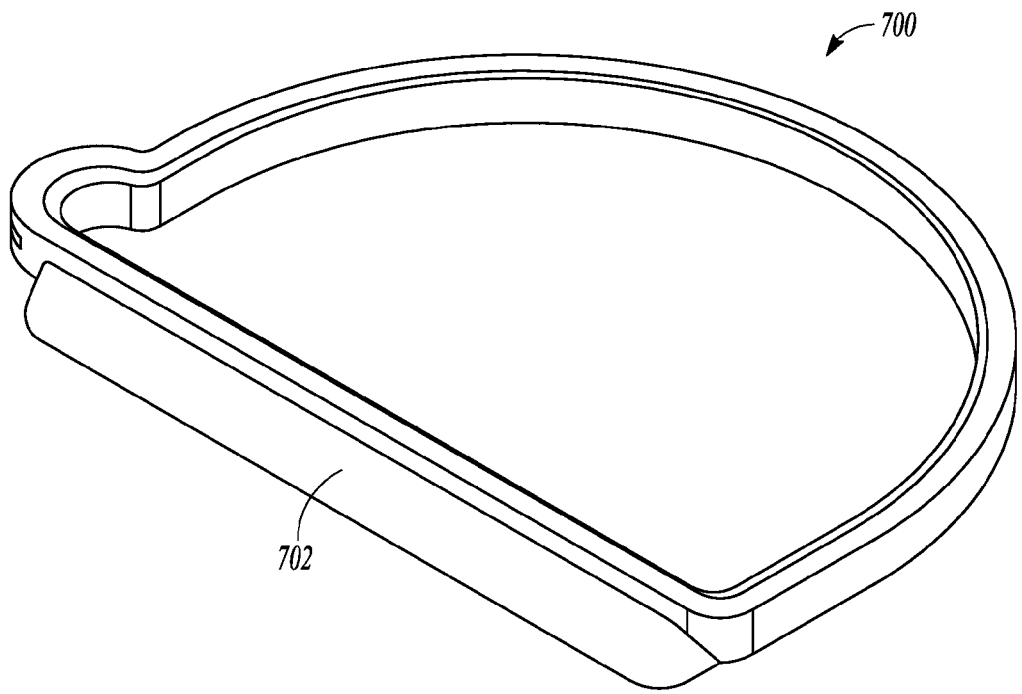
FIG. 12A is a perspective view of an example of a tibial baseplate and fin for use in a unicompartmental knee arthroplasty, in accordance with the present application.
Figure 12B:
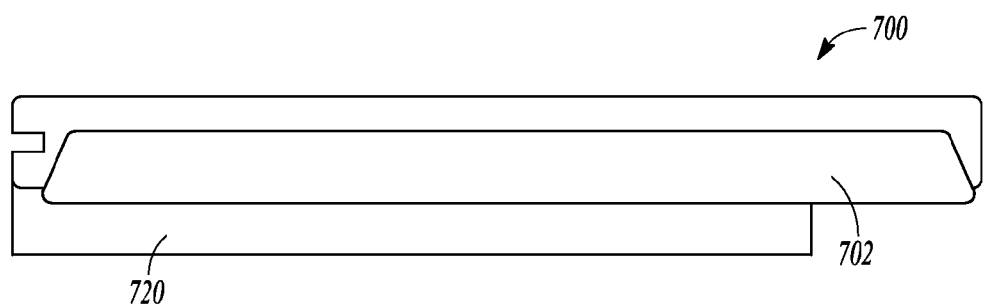
FIG. 12B is a side view of the tibial baseplate and fin of FIG. 12A.

FIGS. 12A and 12B illustrate a tibial baseplate 700 having an intercondylar component 702 and a fin 720 (only shown in FIG. 13B), which can be implanted in a unicompartmental or bi-unicompartmental knee arthroplasty procedure. As similarly described above, the fin 720 can be attached to or integral with an underside of the tibial baseplate 700. The fin 720 can be received in and engage with a slot or channel formed in the tibia in order to mount the tibial baseplate 700 to the tibia. As previously discussed, the fin 720 or the intercondylar component 702 can be comprised of a porous material in some instances to promote bone ingrowth from the resected surface of the tibia. In an example, a tibial baseplate similar to the baseplate 700 can include a fin and exclude an intercondylar component.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A tibial implant configured for attachment to a tibia in a knee arthroplasty, the tibia including a partially resected proximal surface of the tibia includes at least a portion of an intercondylar eminence of the tibia and at least one of an ACL and a PCL, the tibial implant comprising:
a baseplate configured for attachment to the partially resected proximal surface of the tibia and comprising:
a medial compartment;
a lateral compartment; and
an anterior bridge portion between the medial and lateral compartments such that a notch is formed between an inner surface of the medial compartment and an inner surface of the lateral compartment; and
an intercondylar component attachable to or integral with the baseplate, the intercondylar component comprising:
a medial portion shaped to correspond to the inner surface of the medial compartment;
a lateral portion shaped to correspond to the inner surface of the lateral compartment; and
an arcuate portion between the medial portion and the lateral portion and shaped to correspond to the bridge portion of the baseplate;
wherein each of the medial portion, the lateral portion and the arcuate portion have an inner surface, wherein the inner surface of the medial portion and the lateral portion extends both proximal-distal and medial-lateral into the notch and forms a projection into the notch, wherein the projection of the medial portion and the lateral portion is configured to be received in a groove in a base of the intercondylar eminence, and wherein the inner surface of the medial portion, the lateral portion and the arcuate portion is configured to engage in a press-fit with the intercondylar eminence of the tibia when the tibial implant is attached to the tibia.

2. The tibial implant of claim 1, wherein the intercondylar component includes a porous structure.

3. The tibial implant of claim 2, wherein the porous structure includes tantalum.

4. The tibial implant of claim 2, wherein substantially an entirety of the intercondylar component is formed of a porous metal structure.

5. A tibial implant configured for attachment to a tibia in a knee arthroplasty, the tibial implant comprising:
a baseplate comprising:
a medial compartment;
a lateral compartment; and
an anterior bridge portion between the medial and lateral compartments such that a notch is formed between an inner surface of the medial compartment and an inner surface of the lateral compartment; and
one or more fins attachable to or integral with an underside of the baseplate, the one or more fins comprising:
a first fin having a generally trapezoidal cross-sectional shape and extending from the underside of the medial compartment; and
a second fin having a generally trapezoidal cross-sectional shape and extending from the underside of the lateral compartment;
wherein the first fin is configured for engagement with a first channel having a generally trapezoidal cross-sectional shape that is formed in a resected portion of a medial portion the tibia, and wherein the second fin is configured for engagement with a second channel having a generally trapezoidal cross-sectional shape that is formed in a resected portion of a lateral portion of the tibia; and an intercondylar component comprising:
a medial portion configured to connect to an inner surface of the medial compartment of the baseplate;
a lateral portion configured to connect to an inner surface of the lateral compartment of the baseplate; and
an arcuate portion between the medial portion and the lateral portion and configured to connect to the anterior bridge portion of the baseplate;
wherein each of the medial portion, the lateral portion and the arcuate portion have an inner surface, wherein the inner surface of the medial portion and the lateral portion extends both proximal-distal and medial-lateral into the notch and forms a first projection into the notch, wherein the inner surface of the arcuate portion extends at least proximal-distal and anterior-posterior and forms a second projection into the notch, wherein the first projection and the second projection are configured to be received in a groove in a base of the intercondylar eminence, and wherein the inner surface of the medial portion, the lateral portion and the arcuate portion is configured to engage with the intercondylar eminence of the tibia when the tibial implant is attached to the tibia.

6. The tibial implant of claim 5 wherein the one or more fins comprise a porous structure.

7. The tibial implant of claim 6 wherein the porous structure includes tantalum.

8. The tibial implant of claim 1, wherein each of the medial portion, the lateral portion and the arcuate portion is press-fit into the groove.

9. The tibial implant of claim 5, wherein the inner surface of each of the medial portion, the lateral portion and the arcuate portion is press-fit into the groove.

10. The tibial implant of claim 1, wherein the inner surface of the arcuate portion extends at least proximal-distal and anterior-posterior and forms a second projection into the notch.

11. The tibial implant of claim 1, wherein the intercondylar component has an inferior surface and the inner surface extends to the inferior surface, and wherein the projection is of a largest medial-lateral extent into the notch at an intersection of the inner surface and the inferior surface.

12. The tibial implant of claim 5, wherein the intercondylar component has an inferior surface and the inner surface extends to the inferior surface, and wherein the first projection is of a largest medial-lateral extent into the notch at an intersection of the inner surface and the inferior surface.

* * * * *